United States Patent
Khowaylo et al.

(10) Patent No.: US 11,684,467 B2
(45) Date of Patent: Jun. 27, 2023

(54) IN-SITU CURING BIODEGRADABLE ANCHOR WITH REINFORCEMENT

(71) Applicant: Acuitive Technologies, Inc., Allendale, NJ (US)

(72) Inventors: Alex Khowaylo, Upper Saddle River, NJ (US); Michael P. McCarthy, Centre Hall, PA (US); Minh-Tuan Richard Tran, Fort Worth, TX (US); Rui J. Ferreira, Livingston, NJ (US)

(73) Assignee: Acuitive Technologies, Inc., Allendale, NJ (US)

( * ) Notice: Subject to any disclaimer, the term of this patent is extended or adjusted under 35 U.S.C. 154(b) by 808 days.

(21) Appl. No.: 16/347,489

(22) PCT Filed: Nov. 7, 2017

(86) PCT No.: PCT/US2017/060322
§ 371 (c)(1),
(2) Date: May 3, 2019

(87) PCT Pub. No.: WO2018/085807
PCT Pub. Date: May 11, 2018

(65) Prior Publication Data
US 2020/0107927 A1  Apr. 9, 2020

Related U.S. Application Data

(60) Provisional application No. 62/418,535, filed on Nov. 7, 2016.

(51) Int. Cl.
*A61F 2/08*   (2006.01)
*A61B 17/84*  (2006.01)
*A61L 31/12*  (2006.01)

(52) U.S. Cl.
CPC .......... *A61F 2/0811* (2013.01); *A61B 17/846* (2013.01); *A61L 31/127* (2013.01);
(Continued)

(58) Field of Classification Search
CPC ............ A61F 2/0811; A61F 2002/0858; A61F 2210/0004; A61F 2210/0085; A61B 17/846; A61L 31/127
See application file for complete search history.

(56) References Cited

U.S. PATENT DOCUMENTS 5,084,050 A * 1/1992 Draenert ............. A61F 2/30767
606/313
5,261,914 A * 11/1993 Warren .................. A61L 31/04
606/77

(Continued)

FOREIGN PATENT DOCUMENTS

EP      1642601 A2    4/2006
WO   WO 2015/035020   3/2015

OTHER PUBLICATIONS

Tran et al. Recent Developments on Citric Acid Derived Biodegradable Elastomers, 2009, Recent Patents on Biomedical Engineering, vol. 2, No. 3, pp. 1-4 (Year: 2009).*

(Continued)

*Primary Examiner* — Kevin T Truong
*Assistant Examiner* — Diana Jones
(74) *Attorney, Agent, or Firm* — McCarter & English, LLP

(57) ABSTRACT

The present invention provides an anchor system for musculoskeletal applications, e.g., for anchoring tendons or ligaments to bone or anchoring two or more bone sections. The anchor system comprises a substantially solid pre-manufactured distal portion (i.e., anchor component) and a settable, biodegradable composite. The biodegradable com- (Continued)

posite is flowable at the time of delivery and is introduced into the fixation site before or after the anchor component. Both the anchor component and the biodegradable composite may be manufactured from citrate-based polymers.

18 Claims, 4 Drawing Sheets

(52) U.S. Cl.
CPC ............... *A61F 2002/0858* (2013.01); *A61F 2210/0004* (2013.01); *A61F 2210/0085* (2013.01)

(56) References Cited

U.S. PATENT DOCUMENTS

| | | | |
|---|---|---|---|
| 5,350,646 A * | 9/1994 | Armand | H01B 1/122 |
| | | | 429/315 |
| 5,383,932 A | 1/1995 | Wilson et al. | |
| 7,923,486 B2 | 4/2011 | Yang et al. | |
| 8,404,264 B2 | 3/2013 | Ameer et al. | |
| 8,530,611 B2 | 9/2013 | Yang et al. | |
| 8,568,765 B2 | 10/2013 | Ameer et al. | |
| 8,574,311 B2 | 11/2013 | Yang et al. | |
| 8,613,944 B2 | 12/2013 | Yang et al. | |
| 8,758,796 B2 | 6/2014 | Ameer et al. | |
| 8,911,720 B2 | 12/2014 | Ameer et al. | |
| 8,992,967 B2 | 3/2015 | Ameer et al. | |
| 9,145,467 B2 | 9/2015 | Yang et al. | |
| 9,248,147 B2 | 2/2016 | Yang et al. | |
| 9,492,477 B2 | 11/2016 | Yang | |
| 9,611,354 B2 | 4/2017 | Yang et al. | |
| 9,642,933 B2 | 5/2017 | Yang et al. | |
| 9,750,845 B2 | 9/2017 | Ameer et al. | |
| 9,840,583 B2 | 12/2017 | Yang et al. | |
| 10,076,538 B2 | 9/2018 | Yang | |
| 10,106,647 B2 | 10/2018 | Yang et al. | |
| 2002/0095158 A1 | 7/2002 | Dixon et al. | |
| 2003/0012734 A1 * | 1/2003 | Pathak | A61L 31/06 |
| | | | 424/9.6 |
| 2003/0032961 A1 * | 2/2003 | Pelo | A61F 2/3872 |
| | | | 606/301 |
| 2007/0208420 A1 * | 9/2007 | Ameer | A61L 33/068 |
| | | | 435/402 |
| 2007/0224245 A1 * | 9/2007 | Ameer | A61L 27/425 |
| | | | 525/437 |
| 2008/0161864 A1 * | 7/2008 | Beck | A61F 2/0811 |
| | | | 606/326 |
| 2009/0325859 A1 * | 12/2009 | Ameer | C08G 63/685 |
| | | | 524/600 |
| 2010/0023057 A1 * | 1/2010 | Aeschlimann | A61B 17/8004 |
| | | | 606/62 |
| 2013/0006278 A1 * | 1/2013 | Mayer | A61B 17/8645 |
| | | | 606/151 |
| 2013/0096611 A1 | 4/2013 | Sullivan | |
| 2013/0345709 A1 | 12/2013 | Burger et al. | |
| 2015/0272646 A1 | 10/2015 | Russell | |
| 2018/0243078 A1 * | 8/2018 | Jastifer | A61B 17/0401 |

OTHER PUBLICATIONS

Alberto Ambard et al., "Calcium Phosphate Cement: Review of Mechanical and Biological Properties", *Journal of Prosthodontics*, vol. 15, pp. 321-328. 2006.

Richard Tran et al., "Recent Developments on Citric Acid Derived Biodegradable Elastomers", *Recent Patents on Biomedical Engineering 2009*, vol. 2. Aug. 6, 2009.

Dipendra Gyawali et al., "Citrate-based Biodegradable Injectable Hydrogel Composites for Orthopedic Applications", *Biomater Sci.*, vol. 1, Issue 1, pp. 52-64. Jan. 1, 2013.

PCT International Search Report and Written Opinion dated Jan. 18, 2018 in International application No. PCT/US2017/060322.

Australian Examination Report dated Jun. 21, 2022 for Australian Application No. 2017355663.

English Translation of Japanese Office Action dated Sep. 13, 2022 for Japanese Application No. 2019-545726.

* cited by examiner

IN-SITU CURING BIODEGRADABLE ANCHOR WITH REINFORCEMENT

RELATED APPLICATIONS

This application is a 35 U.S.C. § 371 National Stage filing of International Application No. PCT/US2017/060322, filed on Nov. 7, 2017, which claims priority to U.S. Provisional Application Ser. No. 62/418,535, filed on Nov. 7, 2016, the entire contents of which are incorporated herein by reference.

TECHNICAL FIELD

The present invention relates to anchor systems for use in musculoskeletal and other anatomical fixation applications.

BACKGROUND ART

Current bone anchors generally rely on a fixed shape that either threads into or is press fit into a bone substrate, which exerts stress on the area surrounding the anchor placement. This stress prevents the surgeon from placing anchors in close proximity and the bone quality needs to be dense to provide adequate initial fixation. Also, bone is not homogenous and, in the case of conventional fixed geometry anchors, there may be some regions where the anchor may not be intimately compressed against bone, thereby creating a weaker interface. The present disclosure overcomes the limitations/shortcomings of the prior art.

SUMMARY

An object of this invention is to provide an anchor system for use intracorporeally, for example, anchoring tendons or ligaments to bone, anchoring two or more bone sections, or closing a sternotomy. Additional uses of the disclosed anchor system will be apparent to persons skilled in the art.

The disclosed anchor system is advantageously produced from biodegradable citrate-based composites, which can include a solid (or substantially solid) pre-manufactured distal portion (i.e., anchor component). The anchor component may contain or define one or more protrusions/extensions on an outer surface that resist anchor migration. The disclosed protrusions/extensions can include, but are not limited to, barbs, knurls, threads, combinations of the foregoing, or other features of various sizes and geometries that are designed to resist motion in one or several directions. The anchor component can be produced in a variety of shapes, for example, but not limited to, cylindrical, conical or with facets (e.g., hex, triangular, square, or others).

Additionally, the anchor component can incorporate one or more sutures or receptacles for adding sutures or cables.

Before or after the anchor component is introduced into the fixation site, a citrate-based in situ settable, biodegradable composite may be introduced to fill in any voids or openings in the bone around the anchor component and to improve its fixation. The biodegradable composite is flowable at the time of delivery to the fixation site, e.g., a viscous gel, and its flowability facilitates delivery to voids that would be otherwise inaccessible (and potentially unknown to the surgeon). Of note, the disclosed biodegradable composite may be introduced to the fixation site before the anchor is positioned therein, after the anchor is positioned therein, or a combination thereof (i.e., both before and after anchor delivery).

In some embodiments, the present invention is directed to a method of intracorporeally anchoring a device relative to bone that comprises:
  a. creating a bone cavity;
  b. introducing a composite into the bone cavity; and
  c. inserting an anchor component into the bone cavity; wherein the anchor component forces the composite into the small interstices of the bone.

In some aspects, the anchor component defines one or more protrusions. In some aspects, the composite is introduced into the bone cavity before the anchor component. In some aspects, the anchor component is inserted in the bone cavity before the composite.

In some embodiments, the composite comprises a citrate-based polymer, e.g., selected from the group consisting of poly(1,8-octanediol-citrate) (POC), methacrylated POC (mPOC), a crosslinked urethane-doped polyester (CUPE), biodegradable photoluminescent polymer (BPLP), dual-crosslinkable poly(alkylene maleate citrate) (PAMC) and a clickable POC-based elastomer (POC-Click). In some aspects, the citrate-based polymer has been produced by reacting together citric acid, a diol monomer and a double bond presenting monomer. In one embodiment, the composite comprises poly(alkylene maleate citrate) (PAMC).

In some aspects, the composite further comprises calcium phosphate. In some embodiments, the calcium phosphate is a part of a bioceramic. In further embodiments, the bioceramic is selected from the group consisting of hydroxyapatite (HA), beta-tricalcium phosphate (beta-TCP) and bioactive glass.

In some embodiments, the composite is crosslinked in situ, e.g., by a polycondensation reaction or free radical polymerization.

In some embodiments, the composite is biodegradable.

In some aspects, the anchor component is inserted into the bone cavity by an anchor inserter. In some embodiments, the composite hardens and engages the bone and the anchor component. In some embodiments, the composite is applied below the anchor component and on top of the anchor component. In some embodiments, the protrusion pressurizes the composite.

In some aspects of the present invention, the anchor component comprises a citrate-based polymer, e.g., selected from the group consisting of poly(1,8-octanediol-citrate) (POC), methacrylated POC (mPOC), a crosslinked urethane-doped polyester (CUPE), biodegradable photoluminescent polymer (BPLP), dual-crosslinkable poly(alkylene maleate citrate) (PAMC) and a clickable POC-based elastomer (POC-Click). In some embodiments, the citrate-based polymer has been produced by reacting together citric acid, a diol monomer and a double bond presenting monomer. In a specific embodiment, the anchor component comprises poly(alkylene maleate citrate) (PAMC).

In some aspects, the anchor component further comprises calcium phosphate. In further embodiments, the calcium phosphate is a part of a bioceramic, and may, e.g., be selected from the group consisting of hydroxyapatite (HA), beta-tricalcium phosphate (beta-TCP) and bioactive glass.

In some embodiments, the anchor component and the composite are made in whole or in part from the same material.

In some embodiments, the present invention also provides an anchor component device, comprising:
  a. a body; and
  b. a protrusion extending from the body; wherein the protrusion engages with the bone cavity to resist motion.

In some embodiments, the body is cylindrical. In some embodiments, the body has a facet. In some aspects, the cross-sectional diameter of the protrusion is greater than the cross-sectional diameter of the body. In some embodiments, there are three protrusions. In some embodiments, the body is solid.

In some aspects, the anchor component defines a cannula. In some aspects, the body has a cross hole. In some aspects, the body interacts with a suture.

In some embodiments, the anchor component of the invention comprises a citrate-based polymer, e.g., selected from the group consisting of poly(1,8-octanediol-citrate) (POC), methacrylated POC (mPOC), a crosslinked urethane-doped polyester (CUPE), biodegradable photoluminescent polymer (BPLP), dual-crosslinkable poly(alkylene maleate citrate) (PAMC) and a clickable POC-based elastomer (POC-Click). In some embodiments, the citrate-based polymer has been produced by reacting together citric acid, a diol monomer and a double bond presenting monomer. In a specific embodiment, the anchor component comprises poly(alkylene maleate citrate) (PAMC).

In some embodiments, the anchor component further comprises calcium phosphate.

In further embodiments, the calcium phosphate is a part of a bioceramic. In another aspect, the bioceramic is selected from the group consisting of hydroxyapatite (HA), beta-tricalcium phosphate (beta-TCP) and bioactive glass.

Additional features, functions and benefits of the disclosed anchor system are described herein and will be further understood when reviewed in conjunction with the appended figures.

BRIEF DESCRIPTION OF THE DRAWINGS

A more complete understanding of the present disclosure and advantages thereof may be acquired by referring to the following description in consideration with the accompanying drawings, in which like reference numbers indicate like features.

FIG. 2, Panel B depicts a citrate-based biodegradable composite being introduced into the fixation site prior to introduction of an anchor component, according to the present disclosure.

FIG. 2, Panel C depicts an exemplary anchor component being introduced into the fixation site and interacting with the citrate-based biodegradable composite, according to the present disclosure.

FIG. 2, Panel D depicts the anchor component being further introduced into the fixation site and further interacting with the citrate-based biodegradable composite, according to the present disclosure.

FIG. 2, Panel E depicts the fully inserted anchor component interacting with dispersed citrate-based biodegradable composite within the fixation site, according to the present disclosure.

DETAILED DESCRIPTION OF EXEMPLARY EMBODIMENT(S)

Figure 1:
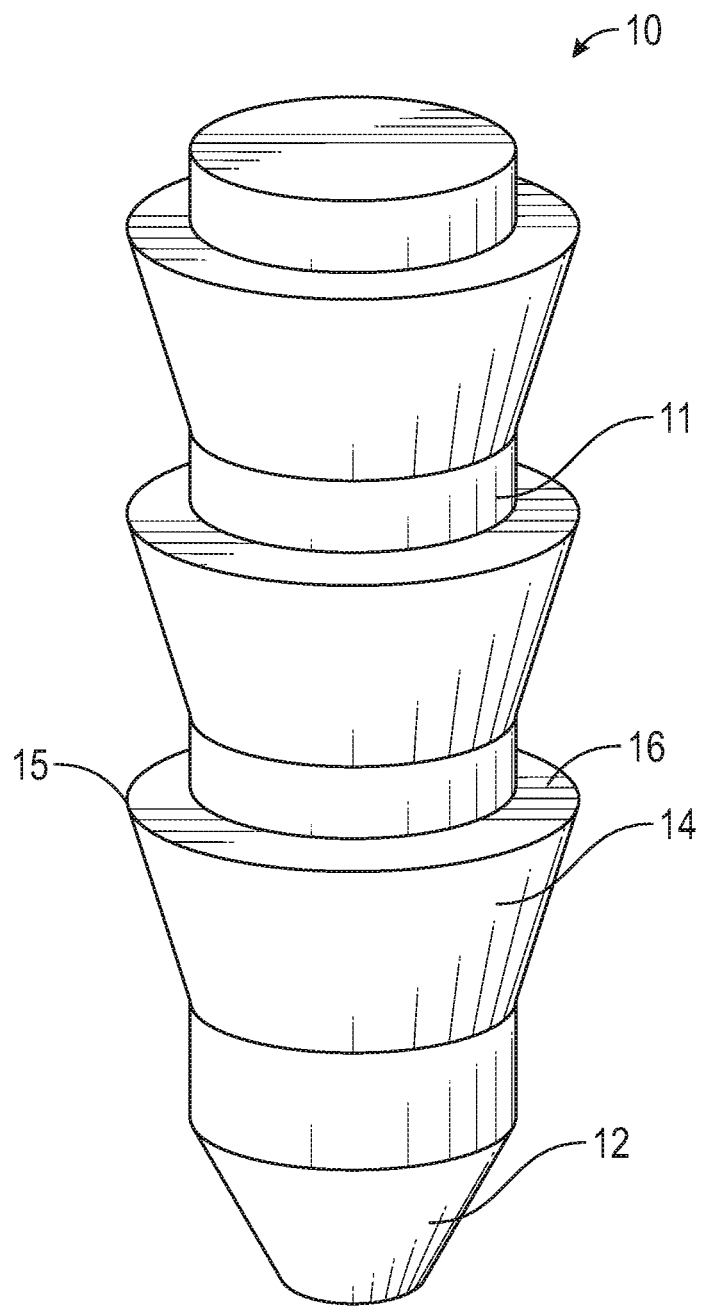
FIG. 1 depicts a front view of an exemplary anchor component according to the present disclosure.

With reference to FIG. 1, exemplary anchor component 10 takes the form of an elongated member that defines a substantially cone-shaped feature 12 at a distal end thereof. The cone-shaped feature 12 functions to position and align anchor component 10 relative to a fixation site. Cone-shaped feature 12 may be integrally formed with or attached to body 11 of anchor component 10. The tapering of cone-shaped feature 12 transitions to a diameter less than the diameter of body 11. In another embodiment, alignment feature 12 has a diameter that is substantially equal to the diameter of the proximal portion of body 11.

In the exemplary embodiment depicted in FIG. 1, body 11 is cylindrical (or substantially cylindrical). However, body 11 may be produced in a variety of shapes, for example, but not limited to, conical or with facets (e.g., hex, triangular, square, or others).

In exemplary embodiments, at least one protrusion 14 is defined on the exterior of body 11. Protrusion 14 may be substantially conical with a cross-sectional diameter greater than the cross-sectional diameter of the adjoining portion of body 11. Protrusion 14 engages the sides of the fixation site with edge 15 functioning to resist motion in one or several directions. In the exemplary embodiment of FIG. 1, three (3) distinct protrusions are defined along the axis of body 11 to enhance fixation of anchor component 10 within a fixation site. Although the plurality of protrusions are of the same dimension in the exemplary embodiment of FIG. 1, the protrusions may have differing diameters, as will be apparent to persons skilled in the art.

In another embodiment, protrusion 14 may define a barb, knurl, thread, or other feature, as will be apparent to persons skilled in the art. As noted above, the quantity of protrusions 14 may vary depending on the surgical requirements (e.g., 1, 2, 3, 4, 5, 6, 7, 8, 9, 10, 11, 12, 13, 14, 15). In one embodiment, at least one protrusion 14 extends the circumference of body 11, as depicted in FIG. 1. In another embodiment, at least one protrusion 14 extends partially around the circumference of body 11. Protrusion 14 can be a separate component that is attached to body 11 or can be a feature created with body 11 (e.g., integrally molded). Protrusion 14 ensures a tight seal within the fixation site and further ensures pressurization of the biodegradable composite (discussed below) is maximized.

Anchor components of the invention, e.g., anchor component 10, can be manufactured from a variety of materials that will be apparent to one of skill in the art. Exemplary materials suitable for manufacturing of the composite may include a polymer, or a polymer composite. In exemplary embodiments, the polymer may be a citrate-based polymer.

As used herein, the term "citrate-based polymer" refers to a polymeric compound produced by reacting citric acid with a diol monomer to generate a polymer having a backbone that comprises hydrolysable ester bond. An exemplary reaction between citrate and a diol monomer is illustrated in Scheme 1 below, wherein HO—R—OH represents a generic diol monomer.

Scheme 1.

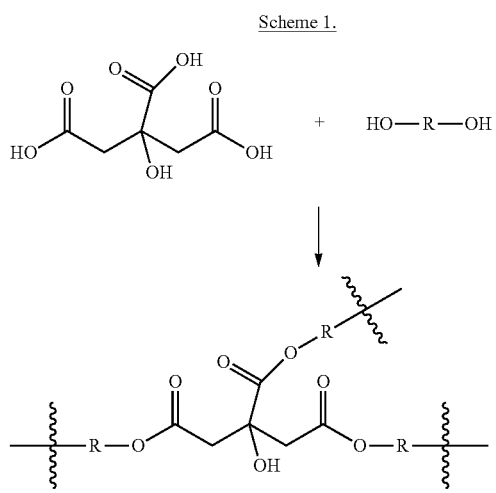

A diol monomer may be any organic substance comprising a diol moiety and capable of reacting with citrate to generate a citrate-based polymer. For example, a diol monomer may be an aliphatic diol comprising from 4 to 12 carbons. In one embodiment, the diol monomer is octanediol. In another embodiment, the diol monomer is dodecanediol.

In some embodiments, the citrate-based polymer may be produced by reacting together citric acid, a diol monomer and a double bond presenting monomer, e.g., unsaturated di-acid. The unsaturated di-acid useful for producing the citrate-based polymer may comprise maleic anhydride, maleic acid, fumaric acid or fumaryl chloride. In one specific embodiment, the diol may comprise poly(ethylene glycol) and the unsaturated di-acid may comprise maleic anhydride. In another specific embodiment, the citric acid useful for producing the citrate-based polymer may be capped with a vinyl group containing monomer, e.g., acryloyl chloride or double bond containing alcohol. The double bonds introduced into the polymer backbone or located on the pendant chains of the polymer backbone via double bond presenting monomers allow formation of a polymer network under mild conditions, e.g., by using free radical polymerization or by ionic cross-linking. In some embodiments, the polymer network formation is formed by a reaction between the double bond presenting monomers and/or the free carboxylic acid with hydroxyl groups present in the citrate-based polymer.

The term "citrate-based polymer" encompasses any citrate-based biomaterial (CBE) as described in, e.g., Tran et al., Citrate-Based Biomaterials and Their Applications in Regenerative Engineering, Annu. Rev. Mater. Res. 2015, 45:277-310; U.S. Pat. Nos. 7,923,486; 8,530,611; 8,574,311; 8,613,944; 8,911,720; 9,145,467; 9,492,477; U.S. Publication No. 2013/0217790; U.S. Publication No. 2016/0075822; U.S. Publication No. 2016/0137776; U.S. Publication No. 2016/0106878 and U.S. Publication No. 2016/0199541, the entire contents of each of which are incorporated herein by reference. For example, the citrate-based polymer may be poly(1,8-octanediol-citrate) (POC), methacrylated POC (mPOC), a crosslinked urethane-doped polyester (CUPE), biodegradable photoluminescent polymer (BPLP), dual-crosslinkable poly(alkylene maleate citrate) (PAMC), or a clickable POC-based elastomer (POC-Click).

The anchor components of the invention, e.g., anchor component 10, may also be manufactured from composites that comprise a citrate-based polymer and calcium phosphate. The calcium phosphate present in the anchor components of the invention may be in the form of free calcium phosphate or a part of a bioceramic. In some embodiments, the calcium phosphate present in the anchor components of the invention is a part of a calcium phosphate cement (CPC) described, e.g., in Ambard and Mueninghoff, Journal of Prosthodontics, Vol. 15, No. 5, pp. 321-328, the entire contents of which are incorporated herein by reference. Exemplary bioceramics that may be included in the in anchor components of the invention may be hydroxyapatite (HA), beta-tricalcium phosphate (beta-TCP) and bioactive glass. The term "bioactive glass", as used herein, refers to a group of glass-ceramic biomaterials comprising one or more of $SiO_2$, CaO, $Na_2O$ and $P_2O_5$. Exemplary non-limiting compositions of the glass-ceramic biomaterials included in the term "bioactive glass" are listed in Table 1 below.

TABLE 1

Bioactive Glass Compositions

| Composition Name | Composition Ingredients |
|---|---|
| 45S5 (Bioglass) | 45 mol % $SiO_2$, 24.5 mol % CaO, 24.5 mol % $Na_2O$ and 6.0 mol % $P_2O_5$ |
| 58S | 60 mol % $SiO_2$, 36 mol % CaO and 4 mol % $P_2O_5$ |
| 70S30C | 70 mol % $SiO_2$, 30 mol % CaO |
| S53P4 | 53 mol % $SiO_2$, 23 mol % $Na_2O$, 20 mol % CaO and 4 mol % $P_2O_5$ |

The anchor components of the invention, e.g., anchor component 10, may be molded into a desired shape from a composition comprising a citrate-based polymer. Additionally, anchor components of the invention, e.g., component 10, can incorporate one or more sutures and/or cables, and/or receptacles for cooperating with sutures or cables.

Exemplary applications for the anchor components of the invention, e.g., anchor component 10, will be more apparent from the following figures and related discussion.

Figures 2A, 2B:
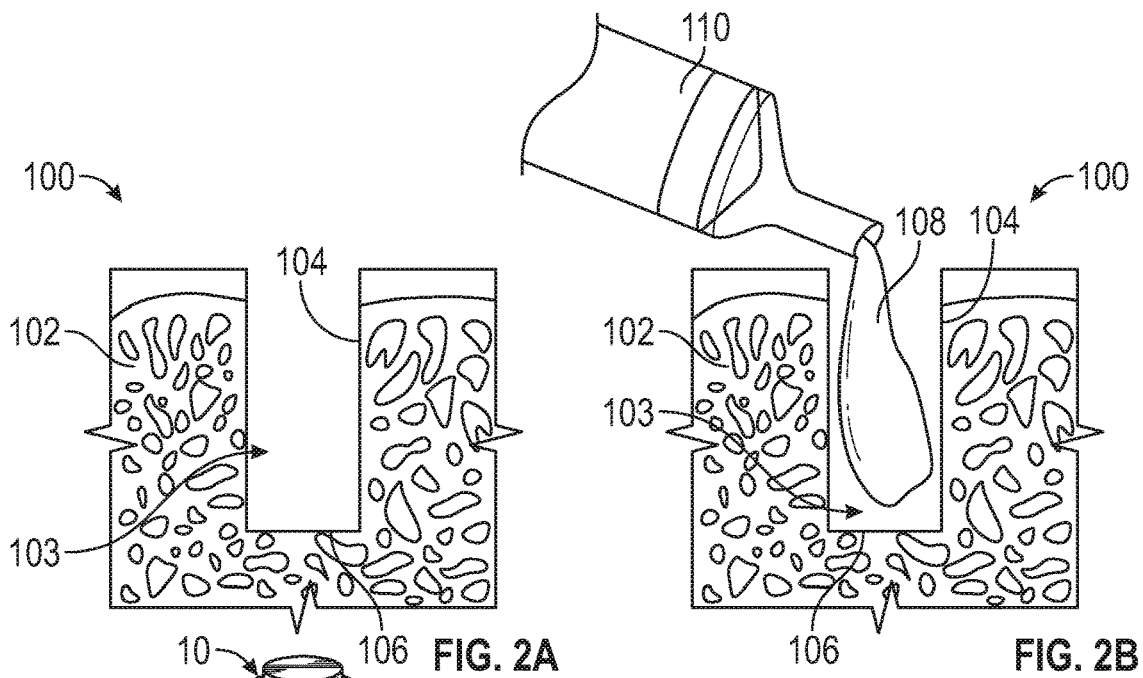
FIG. 2, Panel A depicts a fixation site according to the present disclosure.
Figures 2C, 2D:
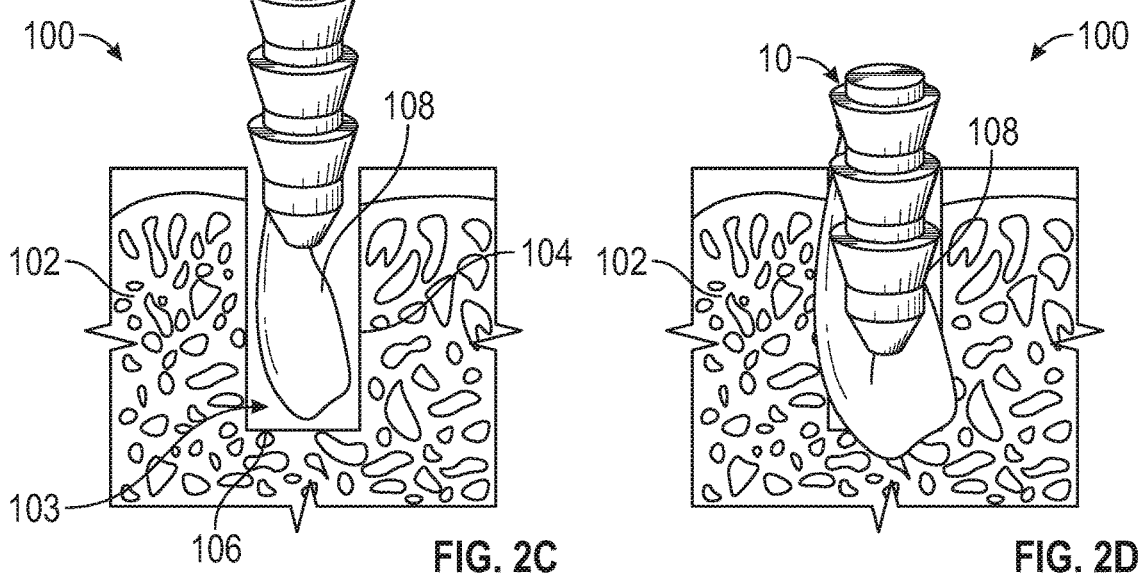
Figure 2E:
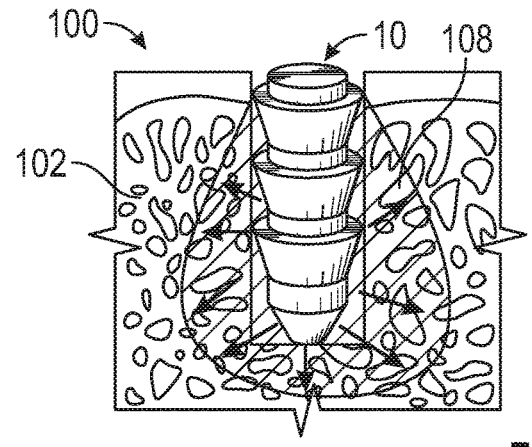

A settable composite of the invention, e.g., citrate-based biodegradable composite, may be introduced into fixation site in addition to the anchor component of the invention. FIG. 2, Panels A-E illustrate an exemplary process that includes, inter alia, introducing a citrate-based biodegradable composite 108 and anchor component 10 into fixation site 103. With specific reference to FIG. 2, Panel A, surgical area 100 includes host bone 102 and fixation site 103. Fixation site 103 generally defines a hole or bone cavity that has been prepped for receiving the anchor component (not shown in FIG. 2, Panel A). The exact diameter of hole 103 is contingent on the surgical requirements; however, hole 103 can be smaller or larger than the cross-section of the protrusions of the anchor component. Host bone 102 can be substantially porous, for example a cancellous bone. Side 104 and bottom 106 of fixation site 103 establish defined limits for inserting the anchor component and pathways for receiving the settable composite (not shown in FIG. 2, Panel A).

The settable composite of the invention may be introduced into fixation site by injection. For example, with reference to FIG. 2, Panel B, citrate-based biodegradable composite 108 is introduced into fixation site 103 by injection syringe 110. The settable composites of the invention, e.g., composite 108, may be manufactured from a variety of materials that will be apparent to one of skill in the art. Exemplary materials suitable for manufacturing the composite may include a polymer, or a polymer composite. In exemplary embodiments, the polymer may be a citrate-based polymer as described hereinabove. For example, the citrate-based polymer comprised in the citrate-based biodegradable composite of the invention may be poly(1,8-octanediol-citrate) (POC), methacrylated POC (mPOC), a crosslinked urethane-doped polyester (CUPE), biodegradable photoluminescent polymer (BPLP), dual-crosslinkable poly(alkylene maleate citrate) (PAMC), or a clickable POC-based elastomer (POC-Click). The settable composites of the invention, e.g., composite 108, may also be manufactured from composites that comprise a citrate-based polymer and calcium phosphate. The calcium phosphate present in the settable composites of the invention may be in the form of free calcium phosphate or a part of a bioceramic. In some embodiments, the calcium phosphate present in the anchor components of the invention is a part of a calcium phosphate cement (CPC). Exemplary bioceramics that may be included in the in anchor components of the invention are hydroxyapatite (HA), beta-tricalcium phosphate (beta-TCP) or bioglass.

The settable composites of the invention, e.g., composite 108, may be introduced into bone cavity 103 to fill the small and irregular openings in the trabecular structure of bone 102 to reinforce the fixation. The specific amount of composite 108 introduced is generally contingent on the volume of fixation site 103; however, enough composite 108 to substantially fill fixation site 103 is preferred.

The composites of the invention, e.g., composite 108, may be prepared from formulations having a variety of viscosities depending on the bioceramic content and/or chemical structure of the polymer comprised in the formulations. The viscosities may range from substantially fluid to substantially thick (e.g., honey consistency) or, in some instances, "doughy" similar to putty. In some embodiments, the anchor component of the invention, e.g., anchor component 10, and the settable composite of the invention, e.g., composite 108, can be made from the same formulation of polymer or polymer composites, different ceramic content, or variations of the disclosed citrate polymer-based materials to synergize the mechanical and degradation properties of the anchor/composite in situ.

With reference to FIG. 2, Panels C-E, as anchor component 10 is driven/introduced into bone cavity 103, anchor component 10 compresses and forces under pressure settable composite 108 into the small interstices of host bone 102. With specific reference to FIG. 2, Panel E, the pressurized settable composite 108 flows according to the path of least resistance, wherein it reinforces those regions surrounding bone cavity 103, and interdigitates with bone 102. Once crosslinked, composite 108 functions to anchor component 10 to bone 102 to provide greater fixation. Indeed, once composite 108 crosslinks or hardens in situ, it can share load over a larger area to reinforce host bone 102 and provide a large surface area to maximize pull out forces required to remove anchor component 10 and provide greater fixation.

Composite 108 may be crosslinked by, but not limited to, polycondensation using heat; free radical polymerization using infrared (IR), ultraviolet (UV), chemical reduction-oxidation (redox), or ultrasound-initiated energy sources to activate the free-radical polymerization; or by ionic crosslinking. In some embodiments, crosslinking in the composite 108 of the invention is achieved by a reaction between the double bond presenting monomers with the free carboxylic and/or hydroxyl groups of the citric acid present in the citrate-based polymer used to prepare the composite. Additional methods for crosslinking of the composite 108 will be apparent to persons skilled in the art.

The protrusions of anchor 10 can be designed to ensure a tight seal and fit within the fixation site 103 to ensure pressurization of composite 108 is maximized.

Figure 3:
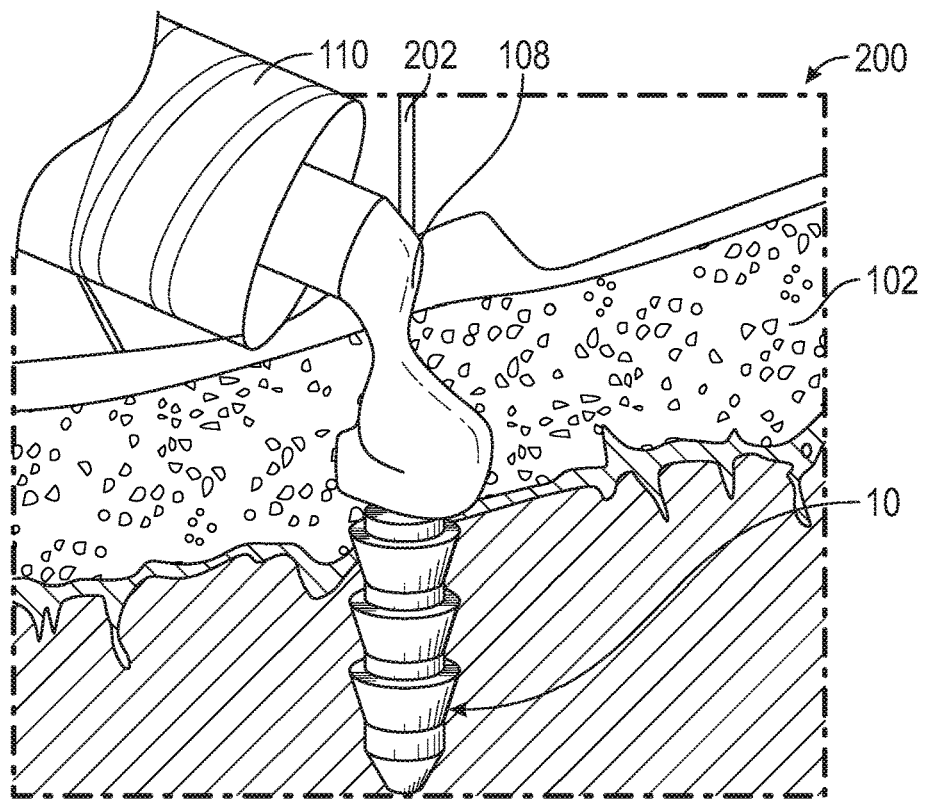
FIG. 3 depicts an exemplary fully anchor component inserted into a fixation site and citrate-based biodegradable composite being introduced on top of the anchor component, according to the present disclosure.

In another embodiment of the present invention, with reference to FIG. 3, surgical area 200 includes host bone 102 and bone cavity (hidden). In this embodiment, anchor component 10 is inserted by anchor inserter 202 into the bone cavity and then settable composite 108 is applied on top of anchor component 10. In one embodiment, the bone cavity can be larger than the cross-section of the protrusion of anchor component 10 so as to allow settable composite 108 to flow alongside anchor component 10. In another embodiment, anchor component 10 can have one or more cross holes to enable the settable composite 108 to flow through anchor component 10.

In another embodiment, the bone cavity is slightly smaller than the cross-section of the protrusions of anchor component 10. Anchor component 10 is press fit into the bone cavity creating a tight seal and settable composite 108 functions to further seal the gap between the top surface of anchor component 10 and the outer edge of the bone cavity of host bone 102.

In another embodiment, anchor inserter 202 and injection syringe 110 can be the same instrument, such that after anchor component 10 is placed, anchor inserter 202 is cannulated and can deliver composite 108 behind the anchor to lock it into host bone 102.

Once crosslinked or hardened in situ, settable composite 108 generally and advantageously integrates with host bone 102 and provides load sharing, as discussed above.

Figure 4:
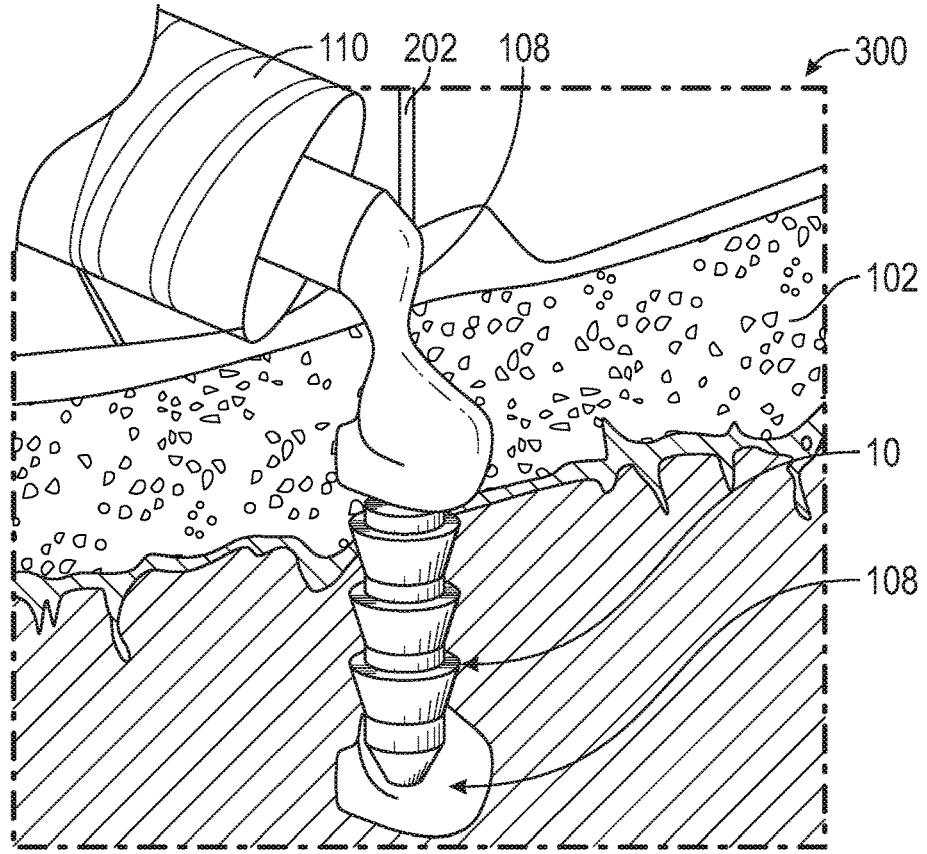
FIG. 4 depicts an exemplary anchor component surround by citrate-based biodegradable composite within a fixation site, according to the present disclosure.

With reference to FIG. 4, in another exemplary embodiment of the present disclosure, surgical area 300 includes host bone 102 and bone cavity (hidden). This embodiment is a combination of several features/functions discussed above with reference to the exemplary embodiments of FIGS. 2A-2E and FIG. 3. In the embodiment of FIG. 4, settable composite 108 is introduced into the bone cavity by injection syringe 110, anchor component 10 is then inserted in the bone cavity and thereafter additional settable composite is applied on top of anchor component 10.

As anchor component 10 is driven into the bone cavity by anchor inserter 202, anchor component 10 compresses and forces under pressure settable composite 108 into the small interstices of host bone 102. The pressurized settable composite 108 flows along the path of least resistance, wherein it reinforces those regions surrounding bone cavity 103, and interdigitates with bone 102 and once crosslinked, anchors to bone 102 to provide greater fixation. Once settable composite 108 crosslinks or hardens in situ, it can share load over a larger area to reinforce host bone 102 and provide a large surface area to maximize pull out forces required to withdraw the anchor and provide greater fixation.

As noted above, settable composites of the invention, e.g., composite 108, may be crosslinked by polycondensation using heat and/or free radical polymerization using infrared (IR), ultraviolet (UV), chemical reduction-oxidation (redox), or ultrasound-initiated energy sources to activate the free-radical polymerization, additional methods will be apparent to persons skilled in the art. Furthermore, the protrusions of anchor 10 can be designed to ensure a tight seal and fit within the fixation site 103 to ensure pressurization of composite 108 is maximized Once anchor component 10 is fully inserted into the bone cavity, an additional amount of settable composite 108 is applied on top of anchor component 10, thereby sealing the gap between the top surface of anchor component 10 and the outer edge of the bone cavity of host bone 102.

The following examples are a non-exhaustive list of methods of use of the disclosed anchor system and associated composite; additional uses will be apparent to persons skilled in the art. The anchor/composite combination can be used to secure sutures to approximate tendons or ligaments to bone, to approximate two or more bone sections to each other, such as a fractured clavicle, or to close a sternotomy. The anchor/composite combination can also be used as a pop rivet to fixate a plate, or as a button to apply compression across a site to stabilize and assist with fusing/healing.

Figure 5:
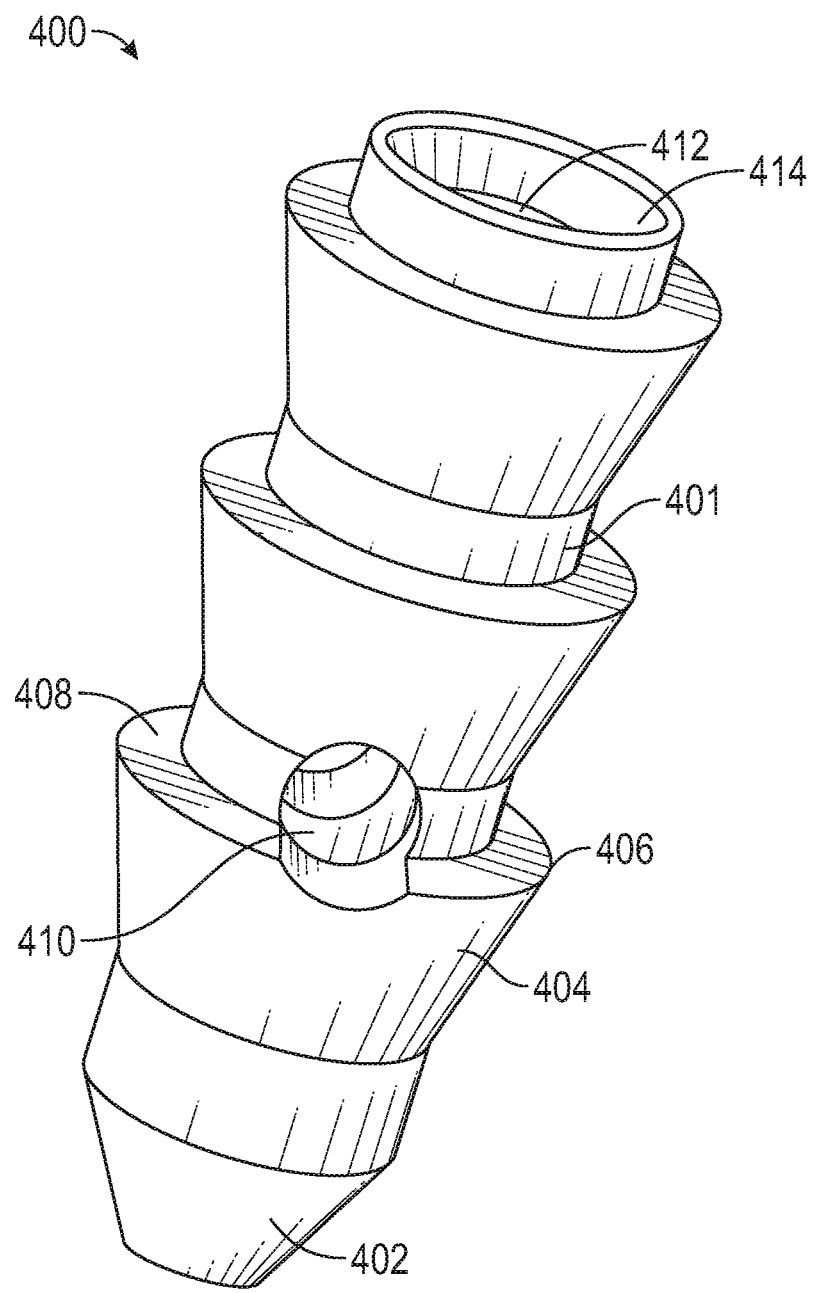
FIG. 5 depicts a front isometric view of an exemplary anchor component with cannulation and cross hole features, according to the present disclosure.

With reference to FIG. 5, exemplary anchor component 400 has a substantially cone-shaped feature 402 that positions and aligns anchor component 400 relative to a fixation site. Cone-shaped feature 402 may be attached to body 401 or integrally formed therewith, and generally tapers to a diameter less than the diameter of body 401 proximal thereto. In another embodiment, cone-shaped feature 402 has a diameter that is substantially equal to the diameter of other portions of body 401. In this embodiment, body 401 is cylindrical; however, body 401 can be produced in a variety of shapes, for example, but not limited to, conical or with facets (e.g., hex, triangular, square, or others). Positioned on the exterior of body 401 is at least one protrusion 404 that is substantially conical with a cross-sectional diameter greater than the cross-sectional diameter of adjacent portions of body 401. Protrusion 404 engages the sides of the fixation site with edge 406 functioning to resist motion in one or several directions.

In another embodiment, protrusion 404 can be a barb, knurl, thread, or other feature, as will be apparent to persons skilled in the art. The quantity of protrusions 404 can vary depending on the surgical requirements (e.g., 1, 2, 3, 4, 5, 6, 7, 8, 9, 10, 11, 12, 13, 14, 15). In one embodiment, at least one protrusion 404 extends the circumference of body 401, as depicted in FIG. 5. In another embodiment, at least one protrusion 404 extends partially around the circumference of body 401. Protrusion 404 can be a separate component that is attached to body 401 or can be a feature created with body 401 (e.g., integrally molded therewith). Protrusion 404 ensures a tight seal within the fixation site and further ensures pressurization of the composite is maximized. Anchor component 400 can be manufactured from a variety of materials, including, but not limited to ceramic, a polymer, or a polymer composite; however, additional materials will be apparent to persons skilled in the art.

Anchor component 400 can be designed with a cannulation 412 and cross hole(s) 410 to allow the settable polymer to flow through it and radiate from its core to interdigitate with the surrounding anatomy. In addition, the settable material can be injected first into the bone cavity for anchor component 400 and then followed by anchor insertion, which will compress the settable material within the cancellous bone bed for enhanced fixation. In exemplary embodiments, anchor component 400 cannulation 412 and cross holes 410 advantageously function to introduce a settable polymer after anchor component 400 is in place, thereby allowing the settable biodegradable polymer to fixate in front of, along the length of and behind anchor component 400 in situ. The viscosity of the settable polymer is sufficiently low to permit flow as needed to reach the desired clinical locations. Additionally, anchor component 400 can incorporate one or more sutures and/or receptacles for adding/interaction with sutures or cables.

Although the present disclosure has been described with reference to exemplary embodiments and implementations thereof, the present disclosure is not limited by or to such exemplary embodiments/implementations. Rather, the devices, systems and methods disclosed herein may be modified, enhanced and/or refined without departing from the spirit or scope of the present disclosure.

The invention claimed is:

1. A method of intracorporeally anchoring a device relative to bone, the method comprising:
   a. creating a bone cavity;
   b. introducing a flowable non-thermoplastic composite into the bone cavity, wherein the non-thermoplastic composite comprises a citrate-based polymer selected from the group consisting of poly(1,8-octanediol-citrate) (POC), methacrylated POC (mPOC), a crosslinked urethane-doped polyester (CUPE), biodegradable photoluminescent polymer (BPLP), dual-crosslinkable poly(alkylene maleate citrate) (PAMC) and a clickable POC-based elastomer (POC-Click); and
   c. pressing an anchor component into the bone cavity, wherein the anchor component comprises a citrate-based polymer selected from the group consisting of poly(1,8-octanediol-citrate) (POC), methacrylated POC (mPOC), a crosslinked urethane-doped polyester (CUPE), biodegradable photoluminescent polymer (BPLP), dual-crosslinkable poly(alkylene maleate citrate) (PAMC) and a clickable POC-based elastomer (POC-Click);
wherein the anchor component forces the non-thermoplastic composite into interstices of the bone wherein the non-thermoplastic composite sets in situ.

2. The method of claim 1, wherein the anchor component defines one or more protrusions.

3. The method of claim 1, wherein the non-thermoplastic composite further comprises calcium phosphate.

4. The method of claim 3, wherein the calcium phosphate is a part of a bioceramic.

5. The method of claim 1, wherein the non-thermoplastic composite is crosslinked in situ.

6. The method of claim 5, wherein the non-thermoplastic composite is crosslinked by a polycondensation reaction.

7. The method of claim 5, wherein the non-thermoplastic composite is crosslinked by free radical polymerization.

8. The method of claim 1, wherein the non-thermoplastic composite is biodegradable.

9. The method of claim 1, wherein the non-thermoplastic composite is applied below the anchor component and on top of the anchor component.

10. The method of claim 1, wherein the anchor component further comprises calcium phosphate.

11. The method of claim 10, wherein the calcium phosphate is a part of a bioceramic.

12. The method of claim 1, wherein the anchor component and the non-thermoplastic composite are made in whole or in part from the same material.

13. The method of claim 1, wherein the anchor component includes:
   a. a body; and
   b. a rigid protrusion intermittently extending from the body;
wherein the rigid protrusion engages with the bone cavity to resist motion.

14. The method of claim 13, wherein the body has a facet.

15. The method of claim 13, wherein a cross-sectional diameter of the rigid protrusion is greater than a cross-sectional diameter of the body.

16. The method of claim 13, wherein the anchor component defines a cannula.

17. The method of claim 13, wherein the body has a cross hole.

18. The method of claim 13, wherein the body interacts with a suture.

* * * * *